United States Patent [19]
Nelson

[11] Patent Number: 4,584,993
[45] Date of Patent: Apr. 29, 1986

[54] WRIST BRACE

[76] Inventor: Ronald E. Nelson, 8710 Central Ave., NE., Blaine, Minn. 55434

[21] Appl. No.: 649,735

[22] Filed: Sep. 12, 1984

Related U.S. Application Data

[63] Continuation-in-part of Ser. No. 395,121, Jul. 6, 1982, abandoned.

[51] Int. Cl.⁴ .............................................. A61F 5/00
[52] U.S. Cl. ................................... 128/77; 128/84 R; 128/87 R
[58] Field of Search ............... 128/75, 77, 84 R, 87 R, 128/87 A, 89 R, 132 R, 133, 157, 165; 273/54 B, 73 R, 188, 189 R, 189 A

[56] References Cited

U.S. PATENT DOCUMENTS

| | | | |
|---|---|---|---|
| 2,794,638 | 6/1957 | Risher et al. | 128/87 A |
| 3,238,939 | 3/1966 | Stubbs | 128/165 |
| 3,327,703 | 6/1967 | Gamm | 128/77 |
| 3,512,776 | 5/1970 | Thomas, Sr. | 128/165 |
| 3,533,407 | 10/1970 | Smith | 128/165 |
| 3,598,408 | 8/1971 | Klose | 128/165 X |
| 3,728,738 | 4/1973 | Andolino | 273/54 B X |
| 3,815,908 | 6/1974 | Hashimoto | 128/165 X |
| 4,183,098 | 1/1980 | Knowles, Jr. | 128/87 R X |
| 4,309,991 | 1/1982 | De Marco | 128/165 |
| 4,366,812 | 1/1983 | Nuzzo | 128/77 |

FOREIGN PATENT DOCUMENTS

3006362 8/1981 Fed. Rep. of Germany ........ 128/77

Primary Examiner—Kyle L. Howell
Assistant Examiner—Angela D. Sykes
Attorney, Agent, or Firm—Burd, Bartz & Gutenkauf

[57] ABSTRACT

A flexible elastic, adjustable wrist brace for use by persons requiring wrist support or protection. The wrist brace offers generalized support to the wrist area as well as lateral support to limit flexure of the wrist. The brace includes a base comprised as a flat sheet member of elastic material formable into a sleeve closely encompassing the wrist with the elastic material in tension. A longitudinal support member is fixed to the base positioned to be located on the inside or proximal portion of the wrist and is formed into a plurality of longitudinal pockets. Flat flexible stay members are located in the pockets to provide lateral support to the wrist. A second, distal support member can be provided. A flexible elastic strap has one end fixed to the base and a free end that is wrapped around the wrist and the base to provide additional support. An anchor strap extends from the base, around the thumb and back to the base where a free end is releasably fastened to the base in order to longitudinally fix the position of the base on the wrist and offer a measure of support to the thumb.

31 Claims, 15 Drawing Figures

WRIST BRACE

CROSS REFERENCE TO RELATED APPLICATION

This application is a continuation-in-part of U.S. application Ser. No. 395,121 filed July 6, 1982, entitled WRIST BRACE, now abandoned.

BACKGROUND OF INVENTION

The invention relates to the field of orthopedic, elastic braces for the limbs and joints of a person, and in particular braces for the wrist for use by athletes and other persons to prevent injury and protect preexistent injury from aggravation.

The wrist presents a complex bone and muscular structure prone to injury upon overexertion or upon unusual lateral movement, rotary movement or hyperextension. Certain sports, such as tennis, are particularly exerting on the wrist. In addition, the wrist may be accidentally traumatically injured and require support. Elastic wrist straps that wrap around the wrist are available but do not give the measure of support that might be needed and are prone to migrate on the wrist. A wrist brace preferably gives good support to the wrist without entirely immobilizing it.

SUMMARY OF INVENTION

The present invention relates to a flexible elastic wrist brace for use by athletes and others requiring wrist support or protection. The wrist brace offers generalized support to the wrist area as well as lateral support to limit flexure of the wrist. The brace includes a base comprised as a flat sheet member of elastic material formable into a sleeve with proximal and distal sides closely encompassing the proximal and distal sides of a wrist with the elastic material in tension. A longitudinal proximal support member is fixed to the base positioned to be located on the inside or proximal portion of the wrist and is formed into a plurality of longitudinal pockets. Flat flexible stay members are located in the pockets to provide lateral support to the wrist. A flexible elastic strap has one end fixed to the base and a free end that is wrapped around the wrist and the base to provide additional support. A second support strap is provided as a further embodiment of the invention. An anchor strap extends from the base, around the thumb and back to the base where a free end is releasably fastened to the base in order to longitudinally fix the position of the base on the wrist and offer a measure of support of the thumb. The brace is adjustable to fit varying sizes of wrists.

DESCRIPTION OF PREFERRED EMBODIMENTS

Figures 1, 2, 3, 4:
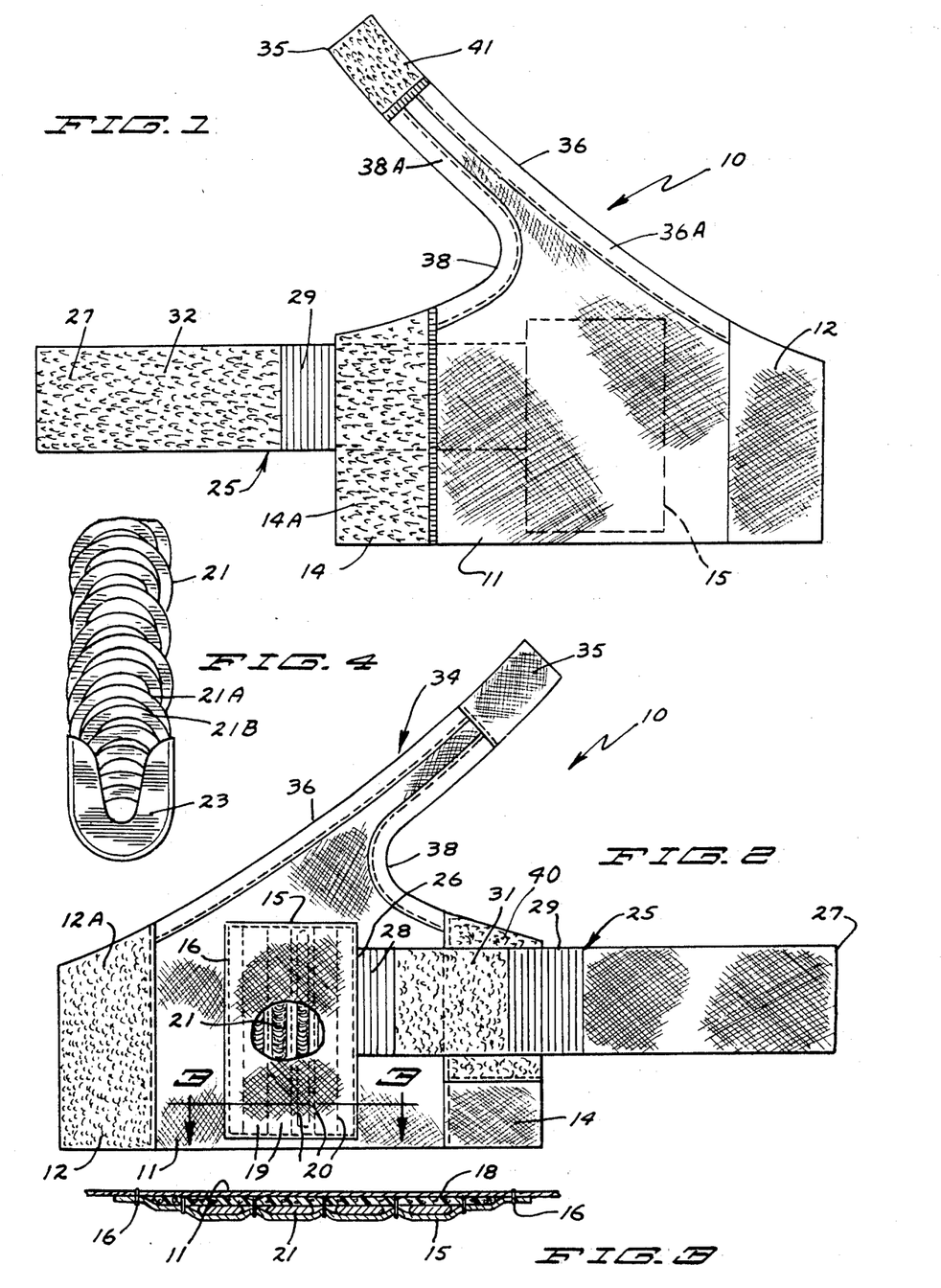
FIG. 1 is a side elevational view of the interior side of a wrist brace according to one form of the invention in unwrapped configuration.
FIG. 2 is a side elevational view of the exterior side of the wrist brace of FIG. 1 in unwrapped configuration.
FIG. 3 is a sectional view of a portion of the wrist brace of FIG. 2 taken along the line 3—3 thereof.
FIG. 4 is an enlarged view of a portion of a flexure stay used in the wrist brace of FIG. 1.

Referring to the drawings, there is shown in FIGS. 1 through 5 a wrist brace according to a first form of the invention indicated generally at 10 having a flat base 11 formable into a sleeve to encompass the wrist. Base 11 is formed of a linearly elastic fabric preferably stretchable in a single direction circumferentially around the wrist. The lateral edges of base 11 are fastened together when the base is in tension and encompassing a wrist. A first fastening strip 12 is fastened along and constitutes a part of a first lateral edge of base 11 by suitable means such as sewing. A second fastening strip 14 is fastened along and constitutes a part of the opposite or second lateral edge of base 11. The fastening strips 12, 14 are formed of synthetic materials that releasably adhere when pressed together, comprised as releasable hook-and-loop type fastening means of the variety sold under the trademark Velcro. The outside surface of the first fastening strip 12 carries first fastening means 12A (see FIG. 2). As shown in FIG. 1, second means 14A are carried on the inside surface of the second fastening strip 14. Overlapping of the means 12A, 14A releasably fastens the fastening strips 12, 14. The fastening strips 12, 14 are coextensive with the lateral edges of base 11. Other suitable fastening means could be used. A proximal support assembly includes a longitudinal, flexible inelastic support member 15 fixed to the outside surface of base 11, or the surface to be orientated away from the skin, and fastened by suitable means such as peripheral stitching 16. Support member 15 is located on base 11 to be positioned on the palmar or proximal wrist side of base 11 when brace 10 is installed on a wrist to limit flexure of the wrist and hand. A resilient foam pad member 18 is located between support member 15 and the surface of base 11 (see FIG. 3). A plurality of elongate, parallel longitudinal pockets 19 are formed between support member 15 and pad 18 by longitudinal parallel seams 20. An elongate flexible support stay member 21 is located in each of the pockets 20. As shown in FIG. 4, each stay member 21 is comprised as a resilient flat stay member that can be flexed in any transverse direction but cannot be compressed longitudinally. The stay member is comprised of two flattened and interleaved helical spring elements 21A, 21B held together by U-shaped end caps 23. Stays 23 provide resistance against flexure of the wrist when brace 10 is installed on a wrist and also inhibit bunching of base 11.

An elongate elastic support strap 25 has one end 26 fixed to base 11 as by sewing adjacent a longitudinal edge of longitudinal support member 15. A free end 27 is extendible around the wrist with base 11 in place on the wrist to offer further wrist support. Strap 25 wraps around the wrist and the support member 15 to firmly secure or press the support member 15 and stay members 21 with respect to the proximal wrist. Strap 25 has a first elastic section 28 and a second elastic section 29 so as to be stretchable in a single direction that is circumferential with respect to the wrist. Means releasably fastening strap 25 in tension around a wrist include releasable hook-and-loop type fastening means. One such means is located at an intermediate section 31 of strap 25 (see FIG. 2) orientated to be outwardly facing when strap 25 engages a wrist. The other means is located on the free end 27 of strap 25, inwardly facing as indicated at 32 in FIG. 1. Overlapping the free end 27 with intermediate section 31 releasably fixes strap 25 in tension around a wrist. The amount of tension is adjustable according to the positioning of free end 27. Support member 15 serves to distribute the tension of strap 25 and avoid bunch up.

An anchor strap 34 extends forwardly from base 11 terminating in a free end 35 configured to be extendible from a proximal side of the hand to the distal side extending between the thumb and index finger. In planar form shown in FIGS. 1 and 2, strap 34 extends at an angle of approximately 45° to base 11 having an elongated gently sloping edge 36 extending from the lateral side of base 11 having first fastening strip 12. Anchoring strap 34 has a second concave or V-shaped edge 38 shaped to wrap around the thumb. Reinforcing strips 36A, 38A are provided on edges 36, 38.

A first anchor strap fastening member is positioned inwardly facing on the free end of anchor strap 34. A second anchor strap fastening member 40 is located outwardly facing in the vicinity of the first lateral edge of base 11. The first and second fastening members can be of synthetic material that releasably adheres when pressed together such that overlapping of the members releasably fastens the free end of the anchor strap to the base.

Figures 5, 6, 7, 8, 9:
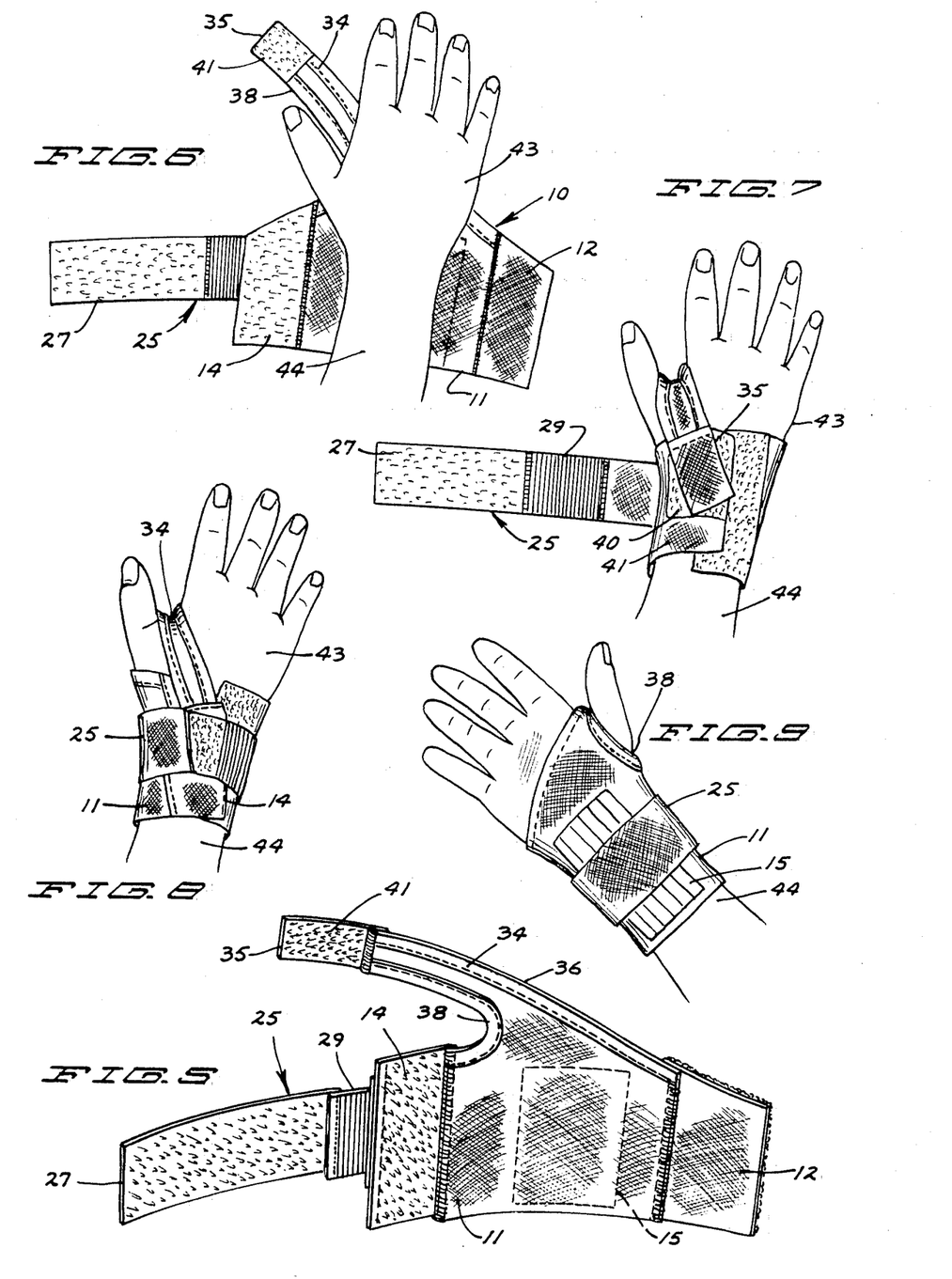
FIG. 5 is a perspective view of the wrist brace of FIG. 1.
FIG. 6 is a view in elevation of the distal portion of a wrist and hand and the wrist brace of FIG. 1 in unwrapped configuration preparatory to installation on the wrist and hand.
FIG. 7 is a view in elevation of the wrist brace of FIG. 6 partially installed on the wrist and hand.
FIG. 8 is a view in elevation of the wrist brace of FIG. 6 completely installed on the wrist and hand showing the distal side of the hand.
FIG. 9 is a view in elevation of the wrist brace of FIG. 6 showing the proximal side of the hand.

Use of the wrist brace 10 is illustrated in FIGS. 6 through 9. In FIG. 6, a hand 43 is poised over the base 10 with the thumb positioned near the concave edge 38 of anchor strap 34. Base 11 and fastening strips 12, 14 are wrapped around the wrist forming a sleeve with longitudinal support member 15 located on the proximal side of the wrist. Fastening strips 12, 14 meet on the distal side of the wrist. Second fastening strip 14 is overlapped over the first fastening strip 12 to releasably hold base 11 in place in tension. Anchor strap 34 is extended between the thumb and index finger. Concave edge 38 of strap 34 generally encompasses the thumb while the elongated sloping edge 36 extends along the proximal portion of the hand (see FIG. 9). First fastening member 41 on the end 35 of anchor strap 34 is engaged with the second fastening member 40 on the exterior surface of second fastening strip 14. It may be seen that fastening strips 12 and 14, as well as the fastening members 40 and 41 are large enough such that varying wrist sizes can be accommodated.

Finally, support strap 25 is wrapped around the base 11 and wrist 44. The fastening means on the inner surface of the free end 27 of strap 25 overlaps intermediate fastening section 31 and releasably adheres to it. The tension in strap 25 is adjustable according to the positioning of the free end 27 on the intermediate section 31. In the fully wrapped configuration of FIGS. 8 and 9, the wrist 44 is well supported and restrained from lateral movement or twisting or the like.

Figure 10:
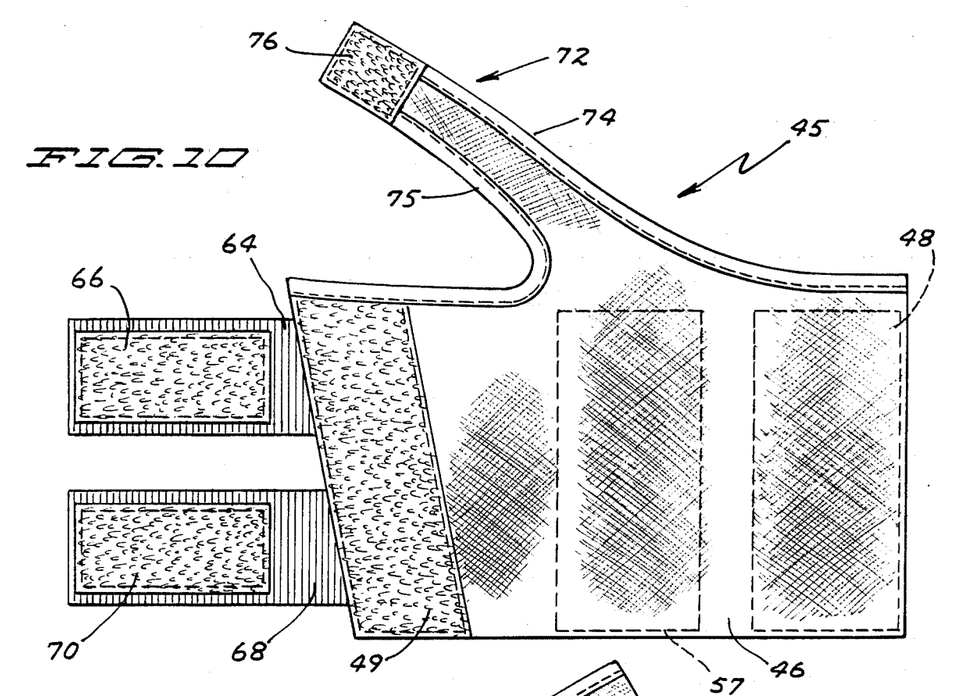
FIG. 10 is a side elevational view of the interior side of a wrist brace according to a second form of the invention in unwrapped configuration.
Figure 11:
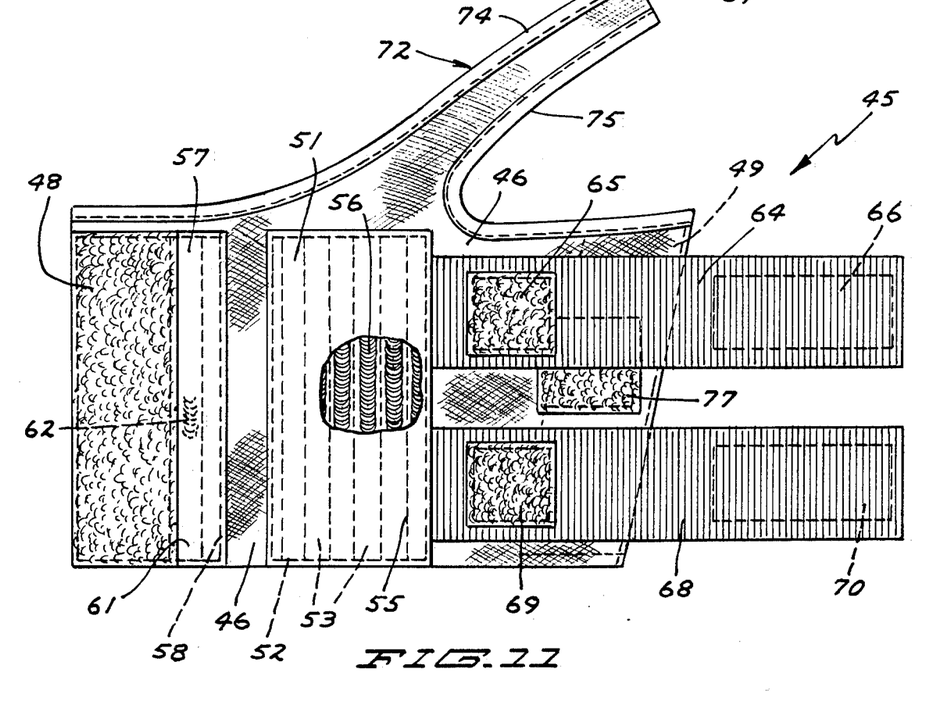
FIG. 11 is a side elevational view of the exterior side of the wrist brace of FIG. 10 in unwrapped configuration.

A wrist brace according to a second form of the invention is shown in FIGS. 10 through 15 and is intended for use when an even greater amount of wrist support is necessary or desirable while not entirely immobilizing the wrist. Brace 45 provides a greater amount of support over a larger area of the wrist and a slightly larger area of the hand. As shown in FIGS. 10 and 11, wrist brace 45 includes a base 46 formed of a linearly elastic material stretchable in a single direction circumferentially around the wrist. Base 46 is configured to be formable into a sleeve to encompass the wrist from a mid-forearm location to a location shortly proximate the point of articulation between the metacarpus and the fingers.

A first fastening strip 48 is secured along a first lateral edge of base 46 as by sewing, and faces outward or away from the wrist when base 46 is installed on a wrist. A second fastening strip 49 is secured along a second opposite edge of base 46 and faces inward. The exposed surfaces of the first and second fastening strips 48, 49 come together when base 46 is wrapped around a wrist. Fastening strips 48, 49 are formed of synthetic materials that releasably adhere when pressed together such as the hook-and-loop type fastening means sold under the trademark Velcro. When base 46 is wrapped around a wrist, second fastening strip 49 is made to overlap the first fastening strip 48 to secure base 46 in a sleeve-like structure wrapped around the wrist and slightly in tension. The outer edge portion of the second lateral edge of base 46 carrying second fastening strip 49 can be inclined as shown in FIG. 10 whereby base 46 is wider at one end than the other for accommodation of the wider hand portion.

A first or proximal support assembly is positioned on base 46 for proximal engagement with the wrist to limit flexure of the wrist and hand, and includes a first longitudinal, flexible inelastic support member 51 fixed to the outside of base 46 fastened thereon by suitable means such as peripheral stitching 52. A resilient foam pad member can be located between support member 51 and the surface of base 46 as previously described. A plurality of elongate, parallel longitudinal pockets 53 are formed by longitudinal parallel seams 55. Each pocket 53 contains an elongate flexible resilient support stay member 56. Each stay member 56 can be comprised as a flat stay member that can be flexed in any transverse direction but cannot be compressed longitudinally such as the stay members earlier described formed of two flattened and interleaved helical spring elements. Such stay members provide resistance against flexure of the wrist and inhibit bunching of base 46.

A second or distal support assembly is positioned on base 46 for distal engagement with the wrist to limit extension of the wrist and hand, and includes a second longitudinal, flexible inelastic support member 57. Second support member 57 is positioned on base 46 by stitching 58 and has a plurality of longitudinal seams which form a plurality of parallel longitudinal pockets 61 each carrying a flexible support stay member 62. Second support member 57 is positioned to be distally located with respect to the wrist and hand when base 46 is wrapped around the wrist. Second upright support member 57 is located partially coextensive on base 46 with the first fastening strip 48. First fastening strip 48 is located on the outside of the corresponding overlapping portion of second upright support member 57.

A first elongate elastic support strap 64 has one end fixed to the base 46 adjacent a longitudinal edge of the first support member 51 and is positioned to be wrapped around the wrist in the vicinity of the lateral articulation of the ulnar and metacarpals. Support strap 64 is stretchable in a single direction that is circumferential with respect to the wrist. A first support strap fastening member 65 is positioned intermediately on strap 64 facing outwardly. A second support strap fastening member 66 is positioned on the free end of strap 64 facing inwardly for engagement with the first fastening member 65 upon being stretched around the wrist. Fastening members 65, 66 can be formed of synthetic materials which releasably adhere when pressed together such as that material sold under the trademark Velcro. When stretched around base 46, first support strap 64 encompasses and enhances the supportive effect of the proximal and distal support assemblies.

A second elongate elastic support strap 68 has a fixed end fixed to base 46 adjacent the longitudinal edge of first support member 51, and a free end stretchable around the wrist for support thereof. Fixing the fixed ends of support straps 64, 68 adjacent the longitudinal edge of support member 51 prevents an undue amount of pull being exerted on the base 46 and provides a secure foundation for the support straps 64, 68. Second support strap 68 is positioned to be wrapped around the wrist at a location further up the arm than the first support strap 64. Second support strap 68 has a first outwardly facing fastening member 69 located intermediate thereon, and a second fastening member 70 located on the free end thereof inwardly facing for overlapping engagement with the first fastening member 69 when being wrapped around the wrist. Fastening members 69, 70 can be formed of synthetic materials that releasably adhere when pressed together. The second fastening members 66, 70 on support straps 64, 68 are relatively elongate permitting some measure of adjustment of the position of the support strap when stretched around the wrist and accordingly the tension in the support strap.

An anchor strap 72 extends forwardly from base 46 terminating in a free end configured to be extendible from a proximal or palmar side of the hand to the distal side extending between the thumb and index finger. In planar form shown in FIGS. 10 and 11, strap 72 extends at an angle of approximately 30 to 40 degrees to base 11 having an elongated gently sloping edge 74 extending from the lateral side of base 46 that carries first fastening strip 48. Anchor strap 72 has a second concave or V-shaped edge 75 shaped to wrap around the thumb. As shown, reinforcing strips are provided on the edges 74, 75.

A first, inwardly facing anchor strap fastening member 76 is located on the free end of strap 72. A second anchor strap fastening member 77 is located on base 46 and is outwardly facing to be distally positioned when base 46 is wrapped around a wrist in order that strap 72 may be extended between the thumb and index finger with the free end thereof positioned to engage second fastening member 77. First and second fastening members 76, 77 can be formed of synthetic materials which releasably adhere when pressed together.

Figures 12, 13, 14, 15:
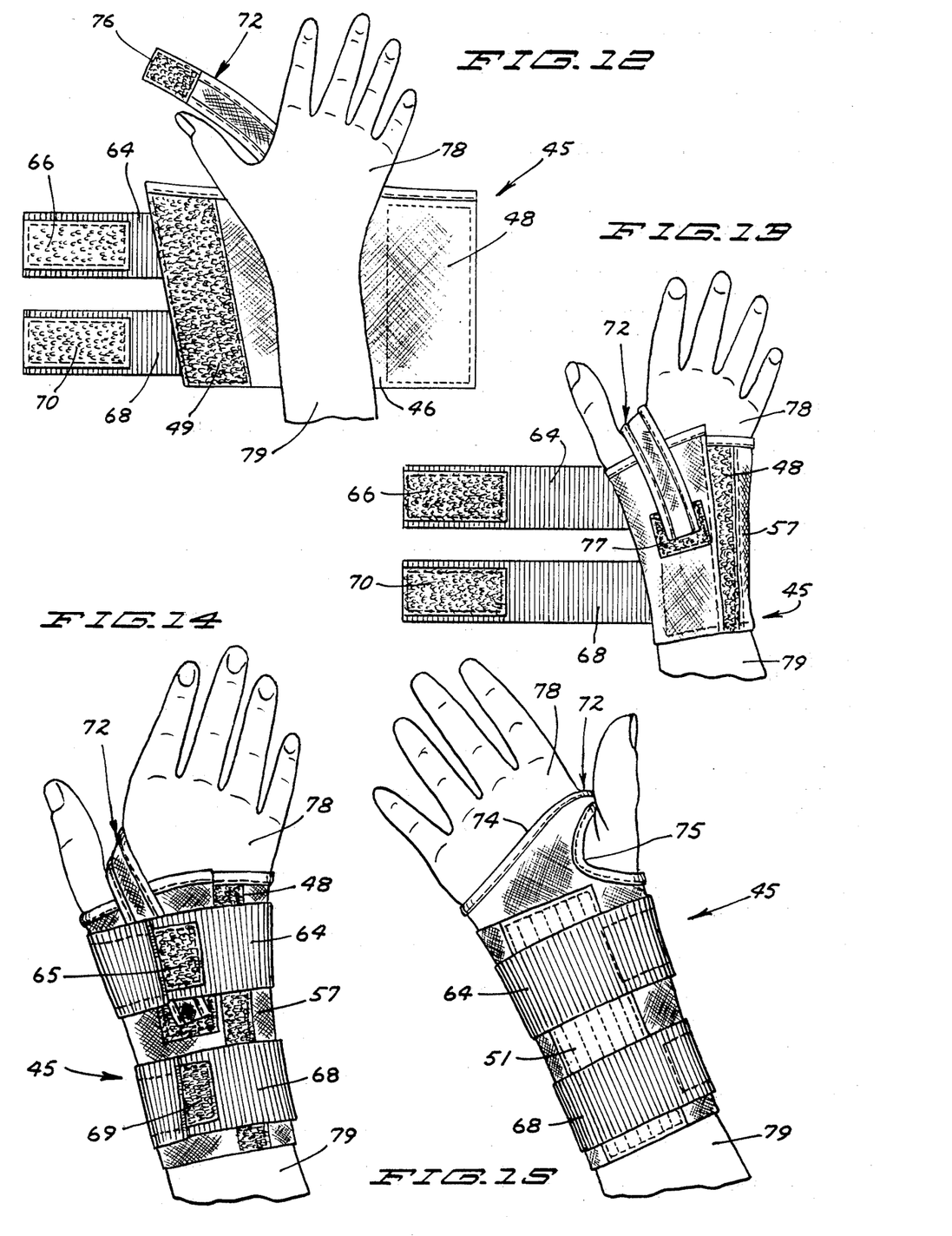
FIG. 12 is a view in elevation of the distal portion of the wrist brace of FIG. 10 in unwrapped configuration preparatory to installation on a wrist and hand.
FIG. 13 is a view in elevation of the wrist brace of FIG. 12 partially installed on a wrist and hand.
FIG. 14 is a view in elevation of the wrist brace of FIG. 12 completely installed on the wrist and hand showing the distal side of the hand.
FIG. 15 is a view in elevation of the wrist brace of FIG. 14 showing the proximal side of the hand.

Use of wrist brace 45 is illustrated in FIGS. 12 through 15. In FIG. 6, a hand 78 is poised over the base 46 with the thumb positioned near the concave edge 75 of anchor strap 72. The other edge 74 of anchor strap 72 is located proximate the outer palmar area or metacarpal area. Base 46 is wrapped around the lower hand portion and adjacent portion of wrist 79 forming a sleeve with the first and second fastening strips being attached on the distal side. When so positioned, the first support assembly contained by first support member 51 is located on the proximal or palmar wrist side to limit flexure of the wrist and hand. The second support assembly carried by the second upright support member 57 is located on the distal or dorsal side to limit extension of the hand and wrist. With the base 46 assembled about the hand and wrist in a sleeve-like relationship, anchor strap 72 is moved between the thumb and index finger to a point where the first anchor strap fastening member 76 engages the second anchor strap fastening member 77 as shown in FIG. 13. This lends some measure of support and serves to prevent migration of the base 46 upward on the wrist. The first and second elongate support straps 64, 68 are then wrapped around the wrist and fastened with the first and second support strap fastening members as shown in FIGS. 14 and 15. The support straps lend support to the hand and wrist but also serve to hold the proximal and distal support assemblies securely in place with respect to the hand and the wrist and the articulation between them.

While there have been shown and described two preferred embodiments according to the invention, it will be apparent that changes and deviations may be had from the embodiments shown without departing from the scope and spirit of the invention.

The embodiments of the invention in which an exclusive property or privilege is claimed are defined as follows:

1. A wrist brace comprising:
   a generally flat base of sheet material adapted to be formed into a tubular sleeve having proximal and distal sides closely conformable to proximal and distal sides of a wrist and formed of elastic material stretchable in a circumferential direction around a wrist;
   a first longitudinal support member fixed on the proximal side of the base for positioning on the proximal side of a wrist when the base is engaged on the wrist;
   said first support member having a plurality of longitudinal pockets, and a plurality of resilient stay members located in the pockets;
   a first flexible elastic support strap having one end fixed to the base adjacent the first support member and a free end extendible in tension around the base and the first support member; and
   means to secure the first support strap in stretched relationship around the base and first support member.

2. The wrist brace of claim 1 including: an anchor strap having one end connected to the base at the proximal side thereof and having a free end extendible between the thumb and the index finger when the base is adapted to be installed on a wrist to a location on the distal side of the base, and means to releasably fasten the free end of the anchor strap on the distal side of the base.

3. The wrist brace of claim 1 wherein: said base has first and second lateral edges that come together on the distal side to form said sleeve, and including means for releasably connecting the first and second lateral edges with the base stretched around a wrist in tension.

4. The wrist brace of claim 3 wherein: said means for connecting the lateral edges comprises first and second fastening strips on the first and second lateral edges carrying hook-and-loop type fastening means.

5. The wrist brace of claim 3 wherein: said anchor strap has a concave edge that generally encompasses the thumb when the free end of the anchor strap is fastened on the distal side of the base.

6. The wrist brace of claim 1 wherein: said first support strap has a first intermediate fastening member carrying outwardly facing fastening means, said free carrying a second fastening member with inwardly facing fastening means to fasten to the outwardly facing fastening means of the first fastening member when the support strap is extended around the base.

7. The wrist brace of claim 6 wherein: said fastening means on the first support strap comprises hook-and-loop type fastening means.

8. The wrist brace of claim 6 wherein: said base has first and second lateral edges that come together to form said sleeve, and including means for releasably connecting the first and second lateral edges with the base stretched around a wrist in tension.

9. The wrist brace of claim 8 including: outwardly facing fastening means on one lateral edge, inwardly facing fastening means on the other lateral edge whereby overlapping of the lateral edges is effective to releasably fasten them together with the base in tension.

10. The wrist brace of claim 9 wherein: the fastening means on the lateral edges of the base comprise hook-and-loop type fastening means.

11. The wrist brace of claim 6 wherein: the fixed end of the first support strap is fixed adjacent a longitudinal edge of the first support member.

12. The wrist brace of claim 6 including: an anchor strap connected to the base at the proximal side thereof and having a free end extendible between the thumb and the index finger when the base is adapted to be installed on a wrist to a location on the distal side of the base, and means to releasably fasten the free end of the anchor strap on the distal side of the base.

13. The wrist brace of claim 12 wherein: said anchor strap has a concave edge that generally encompasses the thumb when the free end of the strap is fastened on the distal side of the base.

14. The wrist brace of claim 12 wherein: means to releasably fasten the free end of the anchor strap on the base comprises inwardly facing fastening means on the free end of the anchor strap, and outwardly facing fastening means located on the distal side of the base.

15. The wrist brace of claim 1 wherein: said resilient stay members are comprised as interleaved and flattened helical spring elements.

16. The wrist brace of claim 15 wherein: said first longitudinal support member is fastened to the base by stitching, said plurality of longitudinal pockets being formed by stitching.

17. The wrist brace of claim 1 including: a second flexible elastic support strap having one end fixed to the base and a free end extendible in tension around the base and the first support member, and means to secure the second support strap in stretched relationship around the base and the first support member.

18. The wrist brace of claim 17 including: an anchor strap having one end connected to the base at the proximal side thereof and having a free end extendible between the thumb and the index finger when the base is adapted to be installed on a wrist, to a location on the distal side of the base, and means to releasably fasten the free end of the anchor strap on the distal side of the base.

19. The wrist brace of claim 18 wherein: means to releasably fasten the free end of the anchor strap on the base comprises inwardly facing fastening means on the free end of the anchor strap, and outwardly facing fastening means located on the distal side of the base.

20. The wrist brace of claim 18 wherein: said first support member is fixed to the outside of the base, the fixed end of each support strap being fixed to the base adjacent a longitudinal edge of the first support member.

21. The wrist brace of claim 20 wherein: each support strap has a first support strap fastening member facing outwardly and positioned intermediately on the support strap, and a second support strap fastening member facing inwardly and positioned on the free end of the support strap for engagement with the first fastening member upon being stretched around the base and the first support member.

22. The wrist brace of claim 18 wherein: each support strap has a first support strap fastening member facing outwardly and positioned intermediately on the support strap, and a second support strap fastening member facing inwardly and positioned on the free end of the support strap for engagement with the first fastening member upon being stretched around the base and the first support member.

23. The wrist brace of claim 18 wherein: said resilient stay members are comprised as interleaved and flattened helical spring elements.

24. The wrist brace of claim 18 wherein: said base has first and second lateral edges that come together on the distal side to form said sleeve, and including means for releasably connecting the first and second lateral edges with the base stretched around a wrist in tension.

25. A wrist brace comprising:
a generally flat base of sheet material adapted to be formed into a tubular sleeve having a proximal side and a distal side closely conformable to proximal and distal sides of a wrist, and formed of elastic material stretchable in a circumferential direction around the wrist;
a first support assembly including a first longitudinal support member fixed on the proximal side of the base for positioning on the proximal side of a wrist when the base is engaged on a wrist;
means forming a plurality of longitudinal pockets between the first support member and the base, and a plurality of resilient stay members located in the pockets for inhibiting wrist flexure when the base is installed upon a wrist;
a second support assembly including a second longitudinal support member fixed to the distal side of the base for positioning on the distal side of the wrist when the base is engaged on a wrist;
means forming a plurality of longitudinal pockets between the second support member and the base, and a plurality of resilient stay members located in the pockets for inhibiting wrist extension when the base is installed on a wrist;

elastic support strap means for encircling the base in tension to press the first and second support assemblies against a wrist when the base is installed on a wrist; and means to secure the support strap means in stretched relationship around the base and the support assemblies.

26. The wrist brace of claim 25 including: an anchor strap having one end connected to the base at the proximal side thereof and having a free end extendible between the thumb and the index finger when the base is installed on a wrist, to a location on the distal side of the base, and means to releasably fasten the free end of the anchor strap on the distal side of the base.

27. The wrist brace of claim 26 wherein: said support strap means includes a first flexible elastic support strap having one end fixed to the base and a free end extendible in tension around the base and the support assemblies, and means to secure the first support strap in stretched relationship around the base; and a second flexible elastic support strap having one end fixed to the base and a free end extendible in tension around the base and the first and second support assemblies, and means to secure the second support strap in stretched relationship around the base.

28. The wrist brace of claim 27 wherein: the fixed ends of the first and second support straps are secured adjacent a longitudinal edge of the first longitudinal support member.

29. The wrist brace of claim 27 wherein: each support strap has a first support strap fastening member facing outwardly and positioned intermediately on the strap, and a second support strap fastening member facing inwardly and positioned on the free end of the strap for engagement with the first fastening member upon being stretched around the base and the support assemblies.

30. The wrist brace of claim 29 wherein: said base has first and second lateral edges that come together to form said sleeve, and including means for releasably connecting the first and second lateral edges with the base stretched around a wrist in tension.

31. The wrist brace of claim 30 wherein: said resilient stay members in the first and second support assemblies are comprised as interleaved and flattened helical spring elements.

* * * * *

UNITED STATES PATENT AND TRADEMARK OFFICE
CERTIFICATE OF CORRECTION

PATENT NO. : 4,584,993

DATED : April 29, 1986

INVENTOR(S) : Ronald E. Nelson

It is certified that error appears in the above-identified patent and that said Letters Patent is hereby corrected as shown below:

Column 1, line 51, "of" in the second instance should be -- to --.

Column 7, line 18, after "free" insert -- end --.

Signed and Sealed this

Twenty-ninth Day of July 1986

[SEAL]

Attest:

DONALD J. QUIGG

Attesting Officer

Commissioner of Patents and Trademarks